(12) United States Patent
Vogt

(10) Patent No.: US 9,901,380 B2
(45) Date of Patent: Feb. 27, 2018

(54) DEVICE FOR STORING AND MIXING BONE CEMENT

(71) Applicant: Heraeus Medical GmbH, Wehrheim (DE)

(72) Inventor: Sebastian Vogt, Erfurt (DE)

(73) Assignee: Heraeus Medical GmbH, Wehrheim (DE)

(*) Notice: Subject to any disclaimer, the term of this patent is extended or adjusted under 35 U.S.C. 154(b) by 446 days.

(21) Appl. No.: 14/571,356

(22) Filed: Dec. 16, 2014

(65) Prior Publication Data

US 2015/0164568 A1 Jun. 18, 2015

(30) Foreign Application Priority Data

Dec. 16, 2013 (DE) .................. 10 2013 226 118

(51) Int. Cl.
*B01F 11/00* (2006.01)
*A61B 17/88* (2006.01)
(Continued)

(52) U.S. Cl.
CPC ...... *A61B 17/8805* (2013.01); *B01F 11/0054* (2013.01); *B01F 11/0082* (2013.01);
(Continued)

(58) Field of Classification Search
CPC ... A61B 17/8805; A61B 17/8822; B29B 7/22; B01F 11/0054; B01F 11/0082;
(Continued)

(56) References Cited

U.S. PATENT DOCUMENTS 3,144,966 A 8/1964 Cook
4,208,133 A 6/1980 Korte-Jungermann
(Continued)

FOREIGN PATENT DOCUMENTS

CA 2855303 A1 1/2015
DE 2808230 A1 8/1979
(Continued)

OTHER PUBLICATIONS

German Office Action for corresponding DE Application No. DE 10 2013 226 118.7 dated Aug. 21, 2014.
(Continued)

*Primary Examiner* — Timothy Cleveland
(74) *Attorney, Agent, or Firm* — Norris McLaughlin & Marcus, P.A.

(57) ABSTRACT

A device and method store, mix, and apply polymethylmethacrylate bone cement, and comprise a first container (51) for a first pasty component of the bone cement, a dispensing plunger (54) that is arranged such that it can be shifted in the first container (51) for pressing the content of the first container (51) through a dispensing tube (62) situated opposite from the dispensing plunger (54), whereby the dispensing tube (62) is arranged such that it can be rotated and shifted in longitudinal direction through a feed-through in a side of the container (51) opposite from the dispensing plunger (54), and a mixing facility (72) for mixing the content of the first container (51), whereby the mixing facility (72) is arranged in the first container (51) and is secured to the dispensing tube (62), such that the mixing facility (72) can be moved in the first container (51) by moving the dispensing tube (62) in order to mix the content of the first container (51), whereby a closure (71) that can be opened is arranged on the end of the dispensing tube (62) pointing into the inside of the first container (51) and closes the dispensing tube (62), and an axially mobile core is arranged in the dispensing tube (62), and a second container for at least one second component of the bone cement is
(Continued)

formed by the space between the closure (71) and the core in the dispensing tube (62), whereby the closure (71) of the second container can be removed from the first end of the dispensing tube (62) through an axial motion of the core and thus the second container can be opened with respect to the first container (51) such that the contents of the second container and of the first container (51) can be mixed with each other in the first container (51), whereby at least one boundary surface of the first container (51) is formed by a mobile volume compensation element (56) and the closure (71) is connected to the dispensing tube (62) by means of a deformable connection (74) such that the closure (71), even when it is open, is connected to the dispensing tube (62) by means of the deformable connection (74).

23 Claims, 5 Drawing Sheets

(51) Int. Cl.
　　B01F 13/00　　　(2006.01)
　　B01F 15/02　　　(2006.01)
　　B29B 7/22　　　(2006.01)
(52) U.S. Cl.
　　CPC ...... B01F 13/0023 (2013.01); B01F 15/0215 (2013.01); B01F 15/0224 (2013.01); B01F 15/0279 (2013.01); B29B 7/22 (2013.01); *B01F 2215/0029* (2013.01)
(58) Field of Classification Search
　　CPC .............. B01F 13/0023; B01F 15/0215; B01F 12/0279; B01F 12/0224; B01F 2215/0029
　　See application file for complete search history.

(56) References Cited

U.S. PATENT DOCUMENTS

| | | | |
|---|---|---|---|
| 4,463,875 A * | 8/1984 | Tepic | A61B 17/8808 206/219 |
| 5,123,927 A | 6/1992 | Duncan et al. | |
| 6,155,812 A | 12/2000 | Smith et al. | |
| 2008/0269909 A1 | 10/2008 | Vogt et al. | |
| 2009/0105144 A1 | 4/2009 | Vogt et al. | |
| 2009/0105366 A1 | 4/2009 | Vogt et al. | |
| 2009/0155923 A1 | 6/2009 | Bonecker | |
| 2010/0046315 A1 | 2/2010 | Merkhan | |
| 2010/0102484 A1 | 4/2010 | Haney et al. | |
| 2011/0104737 A1 | 5/2011 | Bonecker | |
| 2013/0125786 A1 | 5/2013 | Vogt | |
| 2015/0009775 A1 | 1/2015 | Vogt | |

FOREIGN PATENT DOCUMENTS

| | | |
|---|---|---|
| DE | 69614133 T2 | 3/2002 |
| DE | 102007052116 A1 | 4/2009 |
| DE | 102007050762 B3 | 5/2009 |
| DE | 102008030312 A1 | 1/2010 |
| EP | 0861117 B1 | 7/2001 |
| EP | 2072114 A1 | 6/2009 |
| EP | 2596812 A1 | 5/2013 |
| EP | 2823881 A1 | 6/2014 |
| JP | 2015-016331 A | 1/2015 |
| WO | 89/05763 A1 | 6/1989 |
| WO | 2007/053870 A2 | 5/2007 |

OTHER PUBLICATIONS

Australian Examination Report for corresponding AU Application No. 2014203507 dated Jan. 16, 2015.
English Translation of JP Office Action dated Nov. 9, 2015 for corresponding JP Patent Application No. 2014-253850.
English Translation of Chinese Office Action for corresponding Chinese Patent Application No. 2014-10774720.3 dated Jun. 3, 2016.
Chinese Office Action for corresponding Chinese Patent Application No. 2014-10774720.3 dated Jun. 3, 2016.
European Search Report for corresponding EPO Application No. 14189353.7 dated May 8, 2015.
Australian Office Action for corresponding Australian Patent Application No. 2014256326 dated Mar. 15, 2016.

* cited by examiner

DEVICE FOR STORING AND MIXING BONE CEMENT

The invention relates to a device for storing, mixing, and applying polymethylmethacrylate bone cement, and to a method for producing a polymethylmethacrylate bone cement using said device.

Accordingly, the subject matter of the invention is a device for storing and mixing polymethylmethacrylate bone cement that consists, during storage and prior to mixing, of a liquid or pasty first component A and separate powdery or pasty second component B, as well as a method for mixing, and applying if applicable, component A and component B.

Polymethylmethacrylate bone cements (PMMA bone cements) have been in use in medicine for decades for permanent mechanical fixation of total joint endoprostheses. These are based on powder-liquid systems, whereby it is customary to use methylmethacrylate as monomer. Recently, polymethylmethacrylate bone cements that are based on the use of cement pastes have been proposed as well (DE 10 2007 050 762 B3, DE 10 2008 030 312 A1, DE 10 2007 052 116 A1). These bone cements have two cement pastes stored separately in suitable cartridges. These each contain components of a redox initiator system, aside from at least one monomer and suitable polymers.

Methylmethacrylate is the monomer used most commonly in polymethylmethacrylate bone cements. Redox initiator systems usually consist of peroxides, accelerators and, if applicable, suitable reducing agents. Radicals are formed only if all components of the redox initiator systems act in concert. For this reason, the components of the redox initiator system are arranged appropriately in the separate cement pastes such that these cannot trigger a radical polymerisation. The cement pastes are stable during storage. Only when the two cement pastes are mixed to produce a cement dough, the components of the redox initiator system, previously stored separately in the two pastes, react with each other forming radicals which trigger the radical polymerisation of the at least one monomer. The radical polymerisation then leads to the formation of polymers while consuming the monomer, whereby the cement dough is cured. It is customary to use static mixers for mixing the cement pastes and to attach them to the two-component cartridges for this purpose.

When the two cement pastes are pressed out of the cartridges, the two cement pastes are pushed through a static mixer. The processes of pressing out and mixing thus proceed concurrently. Mixing the cement pastes in the static mixer requires a high pressing force since the pressure drop at the mixing elements in the static mixer is very high. It is therefore necessary to use powerful pneumatic or mechanical press-out devices to attain dispensation and mixing of the cement pastes. Said pneumatic or mechanical press-out devices are elaborate from a technical point of view and expensive. A less expensive option are the manually-operated press-out guns, which are customary with the polymethylmethacrylate bone cements based on powder-liquid systems, which are suitable for said cements, but are not sufficiently powerful for pressing-out and mixing bone cement pastes through the use of static mixers.

In conventional two-component cartridges, the volume ratio of component A to component B is 1:1, 1:2, and 1:10. The more the volumes of the components to be mixed through the use of static mixers differ, the more difficult it is to generate a homogeneously mixed bone cement paste. For this reason, very many mixing spirals are needed for larger volume ratios. The larger the number of mixing spirals needed, the larger is the pressure drop in the static mixer during the mixing process. One pasty component A needs to be present, whereas the second component B can be either liquid or powdery or pasty as well.

The Semkit® system is time-proven in the adhesives and sealants industry for many years. It involves storing a paste in a storage container. A second liquid component is present in a stirring rod, separated from the paste through a valve that is integrated into the stirring rod. Actuating the valve allows the liquid to flow into the paste which can then be mixed by hand.

Said system is disadvantageous, though, in that the valve system is suitable for viscous media only. The customary monomer of pasty polymethylmethacrylate bone cements, i.e. methylmethacrylate, cannot be separated permanently from the paste by this valve. Moreover, volume fluctuations arising during the axial mixing motions of the stirring rod in non-compressible pastes are compensated for in this system, firstly, in that the cartridges are soft and, secondly, in that the feed-through for the stirring rod is not absolutely tight such that mixed paste can exit and a small amount of air can also be drawn into the mixed paste. For pasty bone cements, solid cartridges of a stable shape are required, since the very viscous pasty polymethylmethacrylate bone cement can be pressed out of storage containers only through very large press-out forces. Moreover, with bone cements, it is not feasible to use a mixing system, in which an inadvertent exit of small amounts of paste takes place and in which there is the possibility that air is drawn into the paste. This would not only impair the cleanliness in the operating theatre, but also mechanically weaken the cement dough through the introduction of air since air bubbles act as fissure initiation sites in the cured cement and reduce the stability of the cured bone cement. Accordingly, the Semkit® system cannot be used for pasty polymethylmethacrylate bone cements.

Accordingly, it is the object of the invention to overcome the disadvantages of the prior art. In particular, an inexpensive device for storing and mixing polymethylmethacrylate bone cement is to be developed that can be used to store at least one polymethylmethacrylate bone cement component while excluding air, whereby it shall be feasible, after mixing of the cement components, to dispense the cement dough with customary, inexpensive, manually-operated cementing guns. In this context, main component A of the polymethylmethacrylate bone cement shall be a cement paste and the second component can be pasty or preferably be present as a powder. The mixing process must not be associated with any inadvertent leakage of cement dough and no air must be drawn into the cement dough due to volume fluctuations during the mixing process. The device shall also be suitable to ensure safe mixing of the two pastes at a volume ratio of the pastes from 1:10 to 01:30 in order to obtain a homogeneous cement dough. It shall be possible to store the two components of the bone cement separately and to combine them safely by actuating a closure device.

Another aim of the present invention is to ensure that, to the extent possible, no residues from opening or cutting a film open, such as a packaging or a protective film, can remain in the cement dough. The opening, through which the second component is fed into the main component, shall have a reproducible cross-sectional surface area, which, to the extent possible, not change while the components are being mixed. Moreover, the opening of the dispensing tube towards the container, in which the components are being mixed, shall always have a pre-determined cross-sectional surface area. Said cross-sections shall not be subject to any influence, to the extent possible.

It is another object of the invention that the dispensing tube of the device shall be safely patent for the cement dough after the cement components are mixed and the closure is opened, whereby the opening of the dispensing tube must be secured against any blocking by the opened closure while the cement dough is being pressed out. Moreover, a method for mixing pasty polymethylmethacrylate bone cements involving the use of the device to be developed is to be provided.

The objects of the invention are met by a device for storing, mixing, and applying polymethylmethacrylate bone cement, comprising a first container for a first pasty component of the bone cement, a dispensing plunger that is arranged such that it can be shifted in the first container for pressing the content of the first container through a dispensing tube situated opposite from the dispensing plunger, whereby the dispensing tube is arranged such that it can be rotated and shifted in longitudinal direction through a feed-through in a side of the container opposite from the dispensing plunger, and a mixing facility for mixing the content of the first container, whereby the mixing facility is arranged in the first container and is secured to the dispensing tube, such that the mixing facility can be moved in the first container by moving the dispensing tube in order to mix the content of the first container, whereby a closure that can be opened is arranged on the end of the dispensing tube pointing into the inside of the first container and closes the dispensing tube, and an axially mobile core is arranged in the dispensing tube, and a second container for at least one second component of the bone cement is formed by the space between the closure and the core in the dispensing tube, whereby the closure of the second container can be removed from the first end of the dispensing tube through an axial motion of the core and thus the second container can be opened with respect to the first container such that the contents of the second container and of the first container can be mixed with each other in the first container, whereby at least one boundary surface of the first container is formed by a mobile volume compensation element and the closure is connected to the dispensing tube by means of a deformable connection such that the closure, even when it is open, is connected to the dispensing tube by means of the deformable connection.

Preferably, the first component is free of air. Preferably, the second component is powdery or pasty, particularly preferably it is a self-sterilising paste. Self-sterilising pastes can contain, for example, hydrogen peroxide. Preferably, the second container contains a self-sterilising paste of the type described in EP 2 596 812 A1.

Basically, for implementation of the scope of the invention, it is sufficient to have the dispensing tube arranged opposite from the dispensing plunger with respect to the operative connection. A geometrically exact juxtaposition is not required.

A volume compensation element can preferably be implemented through one or two cylinders that are mobile in axial direction in the cylindrical internal space of the first container. Alternatively or in addition, a volume compensation element can just as well be formed through a flexibly deformable skin or membrane.

The invention proposes the closure to be a cap that is plugged onto or arranged on the end of the dispensing tube pointing inside or to be a stopper that is plugged into or arranged on the end of the dispensing tube pointing inside. Said embodiments are particularly easy to implement and therefore are an inexpensive design.

A stopper is preferred according to the invention since it can be combined easily with a securing ring proposed by the invention, which can be slid over the first end of the dispensing tube.

A refinement of the invention proposes the deformable connection to be a fin that is bent when the closure closes the dispensing tube, whereby it is preferred for the fin and the closure to be provided as the same part.

The fin is a connection that is particularly easy and inexpensive to implement. By means of said bent fin, the spring force of an elastic fin can be used to move the closure away from the inner opening of the dispensing tube (on the first end of the dispensing tube).

Moreover, the invention can provide the deformable connection to be tensioned and a spring force to act on the closure such as to move the closure away from the opening of the first end of the dispensing tube, when the closure is detached from the first end of the dispensing tube. In particular, when the closure is detached from the first end of the dispensing tube by moving the core in axial direction.

This can promote or even ensure, if the design is appropriate, that the opened closure does not interfere with the opening into the dispensing tube (on the first end of the dispensing tube). For this purpose, the connection should possess sufficient elasticity with a suitable modulus of elasticity. For example plastic fins approx. 1 mm thick and 3 mm wide made of polyethylene or any other plastic material that is not too hard, for example a common thermoplastic material, are suitable for this purpose.

The invention also proposes a securing element to be arranged on the first end of the dispensing tube pointing towards the inside and the opened closure to be lockable by means of the securing element or to be limited in its mobility with respect to the opening of the first end of the dispensing tube such that the opening of the first end of the dispensing tube can no longer be closed or reduced in size by the closure.

That the opening can no longer be reduced in size by the closure shall mean that the closure cannot become placed in front of or against the opening in any manner in which the flow into the dispensing tube is directly impeded by the closure. The free cross-section of the opening of the dispensing tube at the first end is therefore not reduced in size by the closure secured by the securing element.

It is preferred, according to the invention, to arrange the mixing facility between the securing element and the feed-through on the dispensing tube.

This design ensures that the opened closure does not interfere with the opening into the dispensing tube.

According to a preferred refinement, the invention can provide a strut to be arranged on the securing element such as to be at a distance from the external circumference of the dispensing tube and the strut to bend the fin of the closure in the direction of the second end of the dispensing tube when the securing element is being operated, in particular is being moved. It is particularly preferred to slide the securing element further onto the first end of the dispensing tube and to thus bend the fin by means of the strut and the strut to slide over the fin in the process.

In devices according to the invention comprising securing elements, the invention can provide the securing element to be a securing ring that is plugged onto the first end of the dispensing tube and that projects, in its starting state, beyond said first end and that can be slid further onto the first end of the dispensing tube, whereby sliding the securing ring secures the closure in that the deformability of the deformable connection is limited through the new position of the securing ring.

Preferably, the invention can provide the securing ring a comprise a recess for accommodation of the fin by means of which at least complete bending of the fin towards the opening into the dispensing tube can be prevented. Moreover, the invention can preferably provide at least one snap-in mechanism on the internal circumference of the securing ring that engages an opposite snap-in mechanism on the external circumference of the dispensing tube, whereby the snap-in mechanism prevents the securing ring from detaching from the dispensing tube. It is particularly preferred to provide two snap-in steps, whereby the first snap-in step prevents the securing ring from detaching from the dispensing tube and the second snap-in step prevents the securing of the closure from detaching.

These are options that allow the securing element to be designed in a particularly easy and inexpensive manner.

Moreover, a particularly preferred embodiment of the invention can provide the securing ring to comprise a non-through-going axial recess pointing in the direction of the dispensing tube and, adjacent to it in axial direction in the direction of the front of the device, a radial recess such that the axial recess is bridged by a strut that is situated at a radial distance from the external circumference of the dispensing tube.

Devices according to the invention can be provided appropriately such that the dispensing plunger can be or is locked with respect to the first container, preferably on the end of the first container opposite from the dispensing tube.

The locking allows the dispensing plunger to be held when the first container is being degassed and sterilised.

Moreover, a preferred embodiment of the invention proposes the dispensing tube to be mobile in axial direction by means of a gas-tight feed-through through a boundary of the first container such that the mixing facility can be moved by means of a motion of the dispensing tube in order to mix the content of the first container, whereby the dispensing tube preferably is suspended as in a bearing such that it can be rotated axially.

This prevents air from being introduced. Moreover, the content of the containers is kept sterile by this means.

The mixing facility can be implemented through a plurality of mixing vanes. It is conceivable just as well that the mixing facility can be operated by means of the dispensing tube and, in addition, comprises a separate or integrated magnetic stirring core.

By this means, the content can be mixed easily by hand.

Moreover, the invention can provide the dispensing opening to be closed on the second end of the dispensing tube and it having to be opened before application of the mixed bone cement.

Preferably, the invention can provide a handle on the dispensing tube for manually moving the mixing facility.

The invention can preferably provide the first container to comprise a cylindrical internal space, and the dispensing plunger in the internal space of the first container to be of a shape matching the footprint of the cylindrical internal space.

A cylindrical internal space shall be understood geometrically to mean a general cylinder with any footprint, i.e. not just a cylinder with a circular footprint. The internal space can therefore be a straight cylinder having any footprint, i.e. including a non-circular or round footprint. However, a cylindrical internal space having a circular footprint is preferred according to the invention. Said geometry renders all regions of the first container particularly well-reachable for the mixing facility. The dispensing plunger is then also cylindrical and preferably touches against the walls of the cylindrical internal space of the first container by means of a seal. Particularly preferably, a wiper is arranged on the side of the dispensing plunger facing the internal space and serves to prevent the mixed bone cement paste from being pushed past the dispensing plunger and from exiting on the rear of the device when the dispensing plunger is propelled forward. The mixing facility having the circular cylinder geometry preferred according to the invention has mixing vanes that are equal in size or preferably slightly smaller than the internal diameter of the cylindrical internal space.

The cylindrical geometry with a circular footprint is the simplest for the design of the device. It is particularly preferred that the external surface of the first container also is cylindrical accordingly, and that at least 90% of the wall have an even thickness. Then, the first container can be built laterally as a simple tube.

According to a preferred embodiment, the invention can provide at least one volume compensation element to be arranged in or on the first container such as to be mobile in axial direction, whereby the at least one volume compensation element preferably comprises the gas-tight feed-through through which the dispensing tube is guided in order to operate the mixing facility.

The corresponding structure is easy to realise and can therefore be implemented inexpensively.

According to another simplification, the invention can provide that a volume compensation element is implemented by means of the dispensing plunger and that the motion of the dispensing plunger out of the first container is limited by a boundary element, whereby the boundary element preferably is a snap-in mechanism engaging an opposite snap-in mechanism on the dispensing plunger.

Alternatively, the boundary element can also be provided in the form of a union nut by means of which the dispensing plunger can be affixed. A union nut having a clamping device can be provided on the opposite side and can be used to affix the dispensing tube against the container in the way of a drill chuck.

Using the dispensing plunger as volume compensation element is particularly simple because the dispensing plunger is to be mobile within the first container anyway and/or, more specifically, within the walls of the preferably cylindrical plastic body. Accordingly, same can also be used for volume compensation and no further mobile volume compensation element is required.

Preferably, the invention can provide a volume compensation element to be arranged opposite from the dispensing plunger in the first container as a volume compensation element that is supported as in a bearing such as to be mobile, whereby the volume compensation element preferably comprises the gas-tight feed-through for the dispensing tube.

Just as well, both of the afore-mentioned volume compensation elements can be implemented concurrently in the form of a first volume compensation element that is implemented by means of the dispensing plunger, and a second volume compensation element that is arranged in the first container opposite from the dispensing plunger as a cylindrical volume compensation element that is supported as in a bearing such as to be mobile. In addition, theoretically, a deformable membrane could just as well be provided as third volume compensation element that is capable of taking up a volume change of the first container from operating the mixing facility and/or filling the second component from the second container into the first container. However, it is preferred to be limited to a single volume compensation element in order to simplify the structure.

Arranging the volume compensation element opposite from the dispensing plunger is advantageous in that its mobility can be fully matched to meet the requirements of a volume compensation element.

Moreover, the invention can provide the core as closure element of the dispensing opening of the dispensing tube, whereby the dispensing opening is arranged opposite from the first opening, whereby the core can be taken out of the dispensing tube.

The entire content can be pressed from the second container by the core.

In this context, the invention can provide the core to comprise a wiper on the side facing the first container that wipes off powder or cement dough on the inner surface of the dispensing tube, when the core is being pulled out.

By this means, residues can be prevented from remaining in the dispensing tube, which dissolve during dispensation and thus might impair the properties and the homogeneity of the bone cement. As a result, it can be ensured that the bone cement dispensed early has the same properties as the bone cement dispensed at a later point in time.

Moreover, the invention can provide that at least one volume compensation element is supported as in a bearing through an elastic spring such as to be mobile with respect to the first container, whereby the spring pushes the volume compensation element into the internal space of the first container.

The spring supports the return motion of the volume compensation element. This reduces the forces on the seals and mobile parts of the device caused and transmitted through the also driving hydraulic forces through the bone cement dough and/or its components such that a less expensive structure with thinner materials and lower contact pressures can be implemented.

According to a preferred refinement, the invention can just as well provide the side of the first container having the dispensing tube, or the side through which the dispensing tube is guided, to be closed by a closure cap comprising a feed-through for the dispensing tube that covers a volume compensation element and the closure cap to comprise at least one opening for enabling pressure equalisation between the surroundings and the intervening space between the closure cap and the covered volume compensation element, whereby, preferably, an elastic helical spring for pushing the volume compensation element into the internal space of the first container is arranged between the closure cap and the covered volume compensation element, whereby, particularly preferably, the helical spring is arranged about the dispensing tube.

By this means, impairment of the mobility by external influences (such as, for example, pressure or blockage of the volume compensation element) can be prevented.

The invention can just as well provide the volume compensation element to be locked by a detachable locking means.

This allows an undesired motion of the volume compensation element during the processes of filling or sterilising the first container to be prevented.

The objects underlying the invention are also solved through a method for producing a polymethylmethacrylate bone cement using a device described herein, comprising the procedural steps of:

A) Providing the device, whereby the first container is filled with a first liquid or pasty component of the PMMA bone cement and the second container is filled with a second component of the PMMA bone cement, which preferably is powdery or pasty;

B) Opening the second container by advancing the core in the dispensing tube and dispensing the second component from the second container into the first container through propelling the core further forward in the dispensing tube; and C) Mixing the two components in the first container through moving the mixing facility, whereby moving the mixing facility is associated with the dispensing tube connected to the mixing facility being pushed into and pulled out of the first container repeatedly, whereby the volume change of the content of the first container during the mixing is compensated through a motion of the at least one volume compensation element.

The core seals the device with respect to the outside.

In this context, the invention can provide the core to be removed from the dispensing tube after step B) or after step C), and then a step D) to proceed, in which the mixed bone cement is applied by propelling the dispensing plunger forward in the first container.

This simplifies the application, since the core does not have to be pushed out through propelling the dispensing tube. The application is the final use of the mobile and hand-held device.

Moreover, the invention can provide, while the two components are being mixed in step C), the first end of the dispensing tube pointing into the inside of the container to be pushed all the way onto the dispensing plunger, whereby the pressure operates a securing element that is arranged on said first end and the operation of the securing element locks the opened closure or limits its mobility with respect to the opening of the first end of the dispensing tube appropriately such that the opening of the first end of the dispensing tube can no longer be closed or reduced in size by the closure.

This ensures that the opened closure does not impair the opening and the flow of the cement dough into the dispensing tube.

Moreover, the invention can provide the mixing facility to be connected to the dispensing tube and the content of the first container to be mixed by moving the mixing facility in the first container by moving the dispensing tube into and out of the first container, whereby, in addition, the mixing facility preferably is being rotated by rotating the dispensing tube in the first container.

By this means, the method can be implemented particularly easily, since only one mobile element, i.e. the dispensing tube, is being operated such that the likelihood of incorrect operation is reduced. Moreover, it is easy to mix the components even under adverse conditions outside of an orderly surgical theatre.

Moreover, the invention can provide the first container to get filled with a component of the bone cement before step A) and the inside of the first container to first be degassed and sterilised, whereby the dispensing plunger and/or volume compensation element preferably is/are locked in place for this purpose.

This ensures the sterility of the content. This allows infections of the patient to be prevented.

Moreover, methods according to the invention can be provided accordingly, such that the dispensing tube, after mixing, is moved out in the direction out of the first container such that the mixing facility touches against the inner surface of the volume compensation element or the front inner surface of the container.

By this means, the entire force of the dispensing tube can be utilised to expel the cement dough.

And lastly, the invention can provide the implementation of the method to involve the compensation of volume changes in the container by the volume compensation element.

The invention is based on the surprising finding that the closure being connected to the dispensing tube by means of a connection allows uncontrolled motion and positioning of the closure in the container to be prevented such that inadvertent reduction of or interference with the cross-section of the dispensing tube can be excluded. Moreover, a closure of this type can be designed as a compact volume body in the form of a cap or a plug such that it can be excluded that parts or particles, which might contaminate the bone cement, can possibly detach from the closure.

Using the dispensing tube as the second container is space-saving and also saves an additional mobile part on the inside of the first container. In a design according to the invention, it is sufficient to have a single feed-through by means of which the second container can be opened with respect to the first container and the mixing facility can be operated and the cement dough can be applied.

Moreover, the invention is also based on the surprising finding that the use of at least one mobile volume compensation element allows a gas-tight device for the mixing of PMMA bone cement to be provided, in which no bone cement can exit from the device as a result of the volume changes proceeding during the mixing process. Accordingly, this allows a very simple and inexpensive design for the mixing of bone cement to be implemented, in which there is no danger of contaminating the surroundings with the bone cement and in which there also is no danger of air or gas becoming admixed into the bone cement during the mixing process, which would weaken the bone cement after it is cured.

Using the dispensing tube as actuation facility for the mixing facility and using the dispensing tube as container for the second component of the bone cement allows to forego additional components. This attains further reduction of the cost.

It is essential to the invention that the first container contains a paste or liquid as first component. Moreover, the paste or liquid must not contain any air or gas inclusions and there also must be no supernatant gas phase in the first container. Any gas inclusion can lead to a reduction of the quality of the bone cement thus produced. Due to the paste being incompressible and compressible gas volumes being absent, the content of the first container is fully incompressible. Mixing by sliding in and pulling out the dispensing tube to which the mixing facility is attached is then feasible according to the invention only by means of the volume compensation element. Since the first container has rigid walls, the sliding in or pulling out of the dispensing tube could not proceed otherwise.

The rationale of the invention is therefore based on separating the processes of pressing out and mixing both in time and in space, which is in contrast to the simultaneous combination of the processes of pressing out and mixing through the use of static mixers, which is common with pasty two-component polymethylmethacrylate bone cements. This means that the liquid, pasty and/or powdery components are mixed with each other first and only then the cement dough thus formed is pressed out. The mixing is effected through a mixer to be operated manually in this context. By this means, the press-out force required for dispensing is low and manually operated inexpensive cementing guns can be used to press out the cement dough. Moreover, this also allows for homogeneous mixing of the pastes to be attained even if the pastes have a volume ratio from 1:10 to 1:30. It is essential to the invention to arrange a mobile volume compensation element, which can be used to compensate for volume fluctuations during the mixing process, without any cement dough exiting and without air being drawn into the cement dough.

A particularly preferred embodiment of the invention can provide the closure to be formed by a stopper or a cap as closure that is connected to the dispensing tube by means of a short mobile fin. In this context, the length of the pin must only be such that, after bending the fin into a semi-circle, the stopper or cap can just be plugged into the dispensing tube and/or can just be attached onto the dispensing tube. Once the closure is opened by pushing out the stopper or cap by the core in the dispensing tube, the closure is suspended on the short mobile fin. The end of the dispensing tube has a securing ring situated on it that can be moved axially on the dispensing tube and comprises a recess for accommodation of the fin. In the unopened state, the securing ring is slid only partially over the end of the dispensing tube. After the stopper is pressed out or the cap is pushed off, the securing ring is slid axially in the direction of the dispensing opening of the dispensing tube during the first mixing motion during which the dispensing tube presses against the floor of the dispensing plunger, whereby the dispensing opening becomes situated opposite from the first opening. In this context, the fin is pressed against the dispensing tube in the recess of the securing ring. As a result, only a part of the fin remains mobile. This means, after bending the mobile part of the fin into a semi-circle, the length of the fin is insufficient for the stopper or the cap to become situated in front of the opening of the dispensing tube. As a result, any blockage of the opening of the dispensing tube while the cement dough is being pressed out is fully excluded. Arranging a snap-in element, which becomes effective when slid in axial direction, allows the securing element to be prevented from sliding back into the unsecured state. Advantageously, said embodiment can also provide the securing ring to comprise a first snap-in mechanism that affixes the securing ring on the dispensing tube in the unsecured state such that the securing ring, in the unsecured state, cannot fall off the dispensing tube during storage and/or transport of the device.

An exemplary and, according to the invention, particularly preferred device for storing, mixing, and applying polymethylmethacrylate bone cement is made up of a) a cylindrical storage container having a first space for a first pasty component;

b) a slidable dispensing plunger that can be locked in place on one end of the cylindrical storage container;

c) a dispensing tube;

d) a volume compensation element that is mobile in axial direction in the storage container and possesses a feed-through for a dispensing tube that is slidable in axial direction;

e) a first closure of the storage container on the end of the storage container opposite from the dispensing plunger;

f) a feed-through of the first closure for the dispensing tube that is slidable in axial direction with respect to the storage container;

g) a mixing facility that is attached at the end of the dispensing tube in the space formed between the volume compensation element and the dispensing plunger;

h) a core arranged such as to be mobile in axial direction in the dispensing tube;

i) a second closure of the dispensing tube that can be opened through axial motion of the core in the direction of the dispensing plunger, whereby the second closure is arranged on the end of the dispensing tube at which the mixing facility is situated, whereby the second closure is connected to the dispensing tube by means of a bendable connecting means;

j) a securing ring that can be slid in axial direction on the dispensing tube and contains at least one receptacle for the connecting means of the second closure; and k) a second space for a second component of the bone cement that is formed by the dispensing tube, the second closure of the dispensing tube, and the end of the mobile core pointing towards the inside.

Preferably, the device essentially consists of customary plastic materials for use in medicine, such as polypropylene, polyethylene, polyamide or other plastic materials suitable for application in medicine.

The dispensing tube having the mixing facility arranged on it and the core are based on a cementing system described in EP 2 072 114 B1 which is produced and distributed by the name of Palamix by Heraeus Medical GmbH (Wehrheim).

The pasty first component A is to be stored in the storage container (first container) in the absence of air. This means that there must be no gas phase above pasty component A. As a result, there is no compressible medium that can compensate for increases and decreases in the volume upon the introduction of component B and during the mixing process resulting from the mixer being immersed and pulled out. It is absolutely mandatory to prevent paste from exiting and/or air from being aspirated into the paste during the mixing process.

It is therefore essential to the invention that a volume compensation element is implemented, which preferably is formed by a volume compensation plunger that is mobile in axial direction in the storage container and possesses a recess for feed-through of the dispensing tube. The volume compensation element designed as a mobile plunger can compensate, through axial motion in the direction of the closure, for the volume increase between the dispensing plunger and the volume compensation element due to the introduction of component B into paste A and also the volume added by moving the dispensing tube in the direction of the dispensing plunger. When the dispensing tube moves in the direction of the closure, the decreasing volume between the dispensing plunger and the compensation element is compensated for by the volume compensation element moving in the direction of the dispensing plunger. As a result, mixing is feasible without air entering during the volume increase and without cement paste being able to exit during the temporary volume increase due to the associated pressure increase.

Therefore, according to the invention, the volume compensation element is formed by a plunger that is mobile in axial direction in the storage container and possesses a recess for feed-through of the dispensing tube.

It is feasible to form the volume compensation element from a plunger that comprises a ventilation valve.

Advantageously, the volume compensation element, which rests against the front closure of the cartridge (a lid of the base body), is situated at a distance from the first closure, whereby a helical spring guided about the dispensing tube is preferred.

It is also advantageous to have the volume compensation element secured against sliding before the mixing process by a locking means, whereby it is preferred to have at least one pin that is arranged axially with respect to the dispensing tube (securing pin) and projects through a feed-through of the first closure (the lid of the cartridge) towards the outside and can be or is locked in place on the first closure by means of a snap-in mechanism. This allows the medical user to detach the volume compensation element before the mixing process by removing the securing pin.

Accordingly, the invention can provide the volume compensation element to be secured from sliding by means of a splint, a pin or any other locking means when the storage container is being filled, whereby the splint, pin or other locking means is removed after the filling process or before pasty first component A is mixed with second component B.

Particularly advantageously, said variant can provide the (second) closure to be formed on the first end of the dispensing tube in the form of a stopper that is connected to the dispensing tube by means of a bendable fin, whereby the stopper, in the closed state, is plugged into the dispensing tube. In this context, the length of the fin must only be such that, after bending the fin into a semi-circle, the stopper can just be plugged into the dispensing tube.

The securing ring projects beyond the edge of the dispensing tube, whereby the receptacle of the fin is situated underneath the connecting site of the fin to the dispensing tube or whereby the fin is situated partly in the receptacle.

After the closure is opened and the dispensing tube is attached on the upper side of the dispensing plunger, the securing ring is slid axially in the direction of the cartridge closure (first closure), whereby the fin is pressed in the direction of the dispensing tube by the receptacle of the securing ring and closes the underside of the securing ring against the lower edge of the dispensing tube. As a result, only a part of the fin remains bendable or deformable. The radius of the fin bent into said semi-circle is smaller than in the unsecured state. This means that is impossible, for geometrical reasons, for the stopper to become placed in front of the opening of the dispensing tube. This effectively prevents the opening from being blocked.

In an alternative embodiment of the invention, the volume compensation element is formed by a membrane that can be deformed in axial direction and possesses a recess for feed-through of the dispensing tube.

It is essential for the function of the volume compensation element that the volume compensation element is positioned at a distance from the first closure by means of a spring resting on the first closure, whereby a helical spring that is guided around the dispensing tube is preferred for this purpose. The spring serves to return the volume compensation element back into its starting position after a temporary increase in volume and an ensuing motion of the volume compensation element in the direction of the closure. This means that no negative pressure is needed in the first container to be able to return to the starting position of the volume compensation element.

Accordingly, a device according to the invention can preferably be a cement cartridge for storing, mixing, and applying a two-component cement.

The invention is also implemented by a method for mixing polymethylmethacrylate bone cement using the device according to the invention. In the device according to the invention, a cement paste A is situated in the first container and a component B, separated by means of a membrane, is situated in the second container.

The method can be implemented, for example, through a) moving the core in the dispensing tube in the direction of the stopper, whereby second component B pushes the stopper out of the dispensing tube and the second container gets opened;

b) moving the core further to press component B into pasty component A that is situated in the first container;

c) subsequently mixing second component B and the pasty or liquid first component A to obtain cement dough C by moving the dispensing tube including the mixing facility in axial and/or tangential direction;

d) sliding a securing ring axially onto the dispensing tube until the lower edge of the securing ring is situated flush with the lower edge of the dispensing tube, while the dispensing tube with the mixing facility is being attached to the dispensing plunger during the mixing process;

e) moving the dispensing tube, following successful mixing, in the direction of the closure such that the mixing facility touches against the inner surface of the volume compensation element; and f) then pulling the core out of the dispensing tube and then moving the dispensing plunger in the direction of the first closure, whereby cement dough C is pressed out of the first container through the dispensing tube into the surroundings;

whereby the volume changes of the first container in steps a) through e) are compensated through axial motions of the volume compensation element.

The scope of the invention also includes removing the locking of the volume compensation element before the stopper is being pushed out.

Further exemplary embodiments of the invention shall be illustrated in the following on the basis of five schematic figures, though without limiting the scope of the invention. In the figures.

For simplification, identical or similar components in the figures are identified through the same reference numbers to some extent. Sectioned surfaces are shown by hatching.

Figure 1:
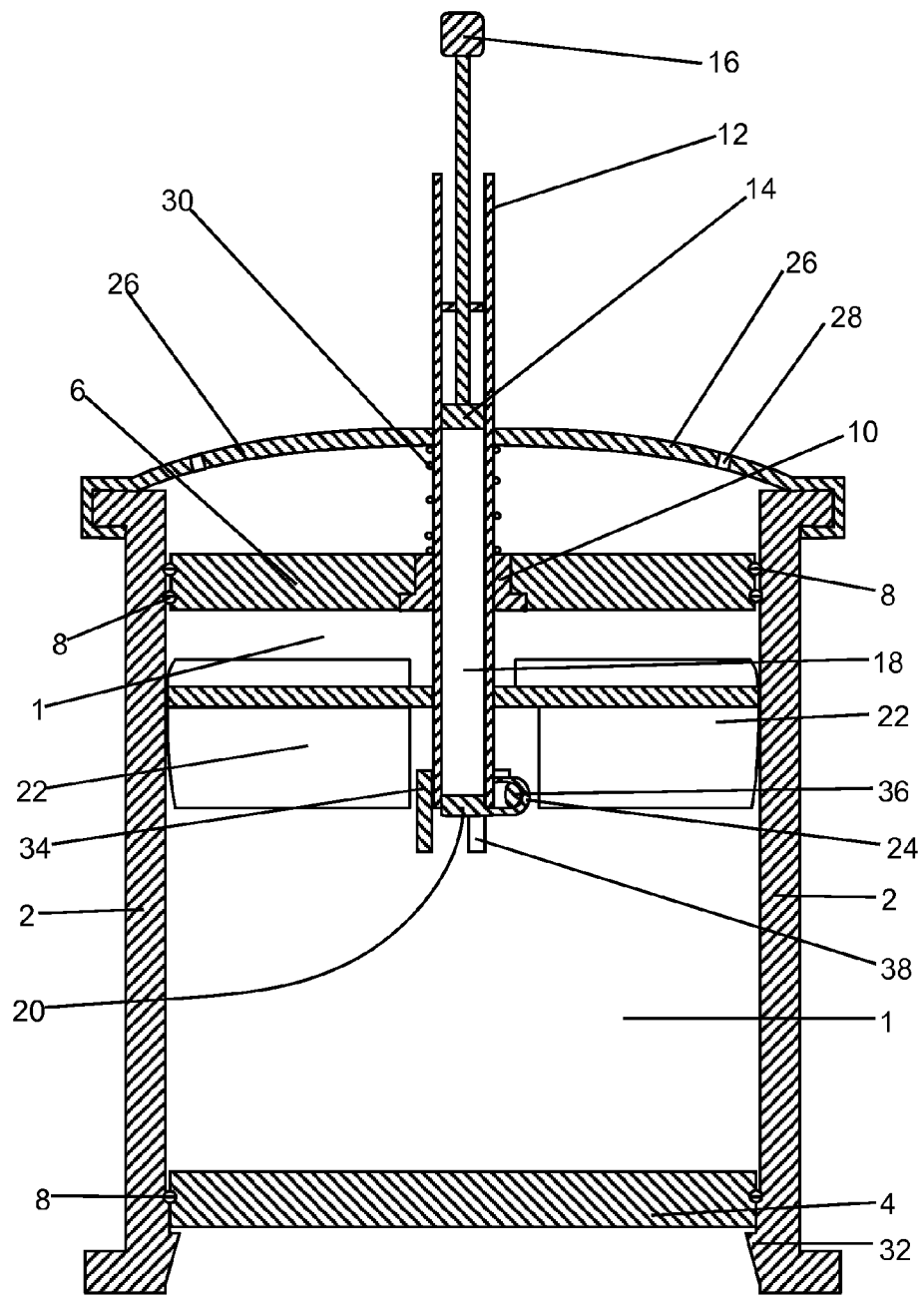
FIG. 1 shows a schematic cross-sectional view of a device according to the invention having a volume compensation element on its front (top)

FIG. 1 shows a schematic cross-sectional view of a device according to the invention. The device has a first container 1 with a cylindrical internal space that is or can be filled with a first component of a PMMA bone cement. The first container 1 contains a pasty mass containing methylmethacrylate monomer as first component. The first container 1 has on its sides the walls 2 of a cylindrical plastic body for its boundaries. On its rear (on the bottom in FIG. 1), the first container 1 has a cylindrical dispensing plunger 4 for its boundary. On its front (on the top in FIG. 1), the first container 1 has a volume compensation element 6 in the form of a cylindrical plunger for its boundary. The dispensing plunger 4 and the volume compensation plunger 6 are arranged in the walls 2 such as to be mobile in the direction of the cylinder axis (from top to bottom in FIG. 1) and are sealed in gas-tight manner with respect to the walls 2 by means of O-rings acting as seals 8.

The volume compensation plunger 6 has a feed-through with a guide sleeve 10 provided in it through which a cylindrical dispensing tube 12 extends. The dispensing tube 12 has a first end extending into the inside of the first container 1 and an opposite second end having a dispensing opening through which a ready-mixed cement dough can be applied. The dispensing tube 12 is arranged in the volume compensation plunger 6 and/or guide sleeve 10 such as to be mobile along the cylinder axis and rotatable about the cylinder axis. The dispensing tube 12 is closed on its inside through a detachable core 14.

The core 14 is connected to a handle part 16 through a rod that extends through the dispensing tube 12 and the dispensing opening. The rod is shown shortened in schematic FIG. 1 and in fact is at least long enough such that the core 14 can be pushed through to the first end of the dispensing tube 12 in order to be able to slide the content of the dispensing tube 12 below it into the first container 1. Moreover, a further cylindrical disc is provided on the rod between the core and the handle part 16 and serves for supporting and stabilising the motion of the rod in the dispensing tube 12. The handle part 16 can be used to move the dispensing tube 12 through the guide sleeve 10 and thus move the dispensing tube 12 in the first container 1.

A second container 18 is arranged in the dispensing tube 12 below the core 14 and is closed on its underside (on the bottom in FIG. 1) by means of a closure 20 in the form of a plug 20. A second component of the bone cement is present in or can be filled into the second container 18. The second component is a pasty mass or a powder. The second component leads to radical curing of the bone cement when it is being mixed with the first component (methylmethacrylate dough). The two components are initially separated from each other by means of the plug 20 and/or closure 20 and the dispensing tube 12.

Mixing vanes 22 are arranged on the outside of the dispensing tube 12 and can be used to mix the content of the first container 1 by moving the dispensing tube 12 in the guide sleeve 10. The mixing vanes 22 thus form a mixing facility 22 for manual mixing of the content of the first container 1. Presently, the mixing vanes 22 are inclined with respect to each other in the way of a propeller.

The plug 20 is connected to the first end of the dispensing tube 12 by means of a bent and tensioned fin 24. The second container 18 can be opened by pushing the core 14 in the direction of the first container 1 into the dispensing tube 12. The content of the second container 18 (the second component) transfers the pressure to the plug 20 until the plug 20 detaches and is tilted and/or moved away from the opening on the first end of the dispensing tube 12 by the tensioned fin 24.

The two fluid components are present in the two containers 1, 18 in the absence of air inclusions and/or are introduced into them without any air or gas inclusions. If the second component is a powder, the intervening spaces contain gas, preferably a sterile or sterilising gas. Moreover, the interior of the containers 1, 18 is degassed and sterilised before being filled. Since there is no gas present on the inside of the first container 1, the content of the first container 1 is incompressible. Accordingly, the volume of the content of the first container 1 changes when the dispensing tube 12 is pushed in or pulled out. The volume compensation can be effected through an axial motion of the volume compensation plunger 6 and, if desired and designed appropriately, through an axial motion of the dispensing plunger 4. As a result, the content of the first container 1 can be mixed without the content of the first container 1 exiting or air being drawn into the first container 1.

On the front (on the top in FIG. 1), the external cylindrical plastic body 2 is closed by means of a lid 26. Openings 28 are provided in said lid 26 to allow air to escape from the intervening space between the lid 26 and the volume compensation plunger 6. It is feasible to forego the openings 28 such that said intervening space can act as a gas spring. However, it is preferred to have a steel spring 30 arranged between the lid 26 and the volume compensation plunger 6 to act as a restoring element. When the volume compensation plunger 6 is being pushed in the direction of the lid 26 as a result of the dispensing tube 12 being slid into the first container 1, the steel spring 30 helps pushing the volume compensation plunger 6 back in the direction of the dispensing plunger 4, when the dispensing tube 12 is being pulled out of the first container 1 again. A locking means (not shown) can be provided in order to block the volume compensation plunger 6 such that the volume compensation plunger cannot move when the first container 1 gets filled with the first component. The locking means can be detached manually before filling the second component into the first container 1 or before mixing the two components in the first container 1.

The rod, by means of which the core 14 is connected to the handle part 16, should be long enough (i.e. longer than shown in schematic FIG. 1 and FIGS. 2, 3, and 4) to allow the second component to be slid into the first container 1. This can ensure that the entire content of the second container 18 can be transferred into the first container 1. A wiper lip (not shown) provided on the lower edge of the core 14 can be used to make sure that the entire content of the second container 18 can be removed from the dispensing tube 12 without leaving any residues.

The underside of the plastic body 2 has snap-in elements 32 arranged on it which can be used to make sure that the dispensing plunger 4 cannot be pushed downwards, out of the plastic body 2. These are briefly lowered into the wall while the dispensing plunger 4 is slid in and/or the snap-in elements 32 briefly deform the seal 8 and, if applicable, even the dispensing plunger 4. A small projection leading to more pronounced compression of the seals 8 of the dispensing plunger 4 can be provided on the underside of the walls 2 just as well.

A securing ring 34 is slid onto the first end of the dispensing tube 12. A snap-in mechanism (not shown) on the securing ring 34 and an opposite snap-in mechanism (not shown) on the dispensing tube 12 ensure that the securing ring 34 can only be slid further onto the first end of the dispensing tube 12 and cannot inadvertently detach from the first end of the dispensing tube 12.

One side of the securing ring 34 (on the right side in FIG. 1) comprises a strut 36 that bridges a radial recess on the inner surface of the securing 34. The fin 24, by means of which the plug 20 is secured to the dispensing tube 12, is bent around said strut 36 on the outside. The radial recess on the inner surface of the securing ring 34 bridging the strut 36 is wide enough and deep enough such that it can accommodate and bend the fin 24. Multiple extension pins 38 are provided on the side of the securing ring 34 facing the dispensing plunger 4 and project in the direction of the dispensing plunger 4 beyond the first end of the dispensing tube 12. Accordingly, the securing 34 has an axial recess between two extension pins 38, which extends in the direction of the dispensing plunger 4 (on the right side in FIG. 1), through which the fin 24 extends.

When the content of the second container 18 is being pushed into the first container 1 by the core 14, the dispensing tube 12 is also moved in axial direction in order to mix the two components. When the dispensing tube 12 is being pushed to the dispensing plunger 4, the securing ring 34 is slid onto the dispensing tube 12 until the ends of the extension pins 38 are flush with the first end of the dispensing tube 12. In this context, the strut 36 slides over the fin 24 and bends the fin such that it touches, at least in part, against the external wall of the dispensing tube 12 and extends from its connection to the dispensing tube 12 in the direction of the front of the device (on the top in FIG. 1).

Preferably, a second opposite snap-in mechanism (not shown) is provided that engages the snap-in mechanism of the securing ring 34 such that the securing ring 34 remains in said slid-in position. What this achieves is that the opened plug 20 can no longer move to the opening of the dispensing tube 12 at the first end thereof and thus close the opening or restrict its free cross-section and thus render a possible flow into the dispensing tube 12 more difficult.

Figure 2:
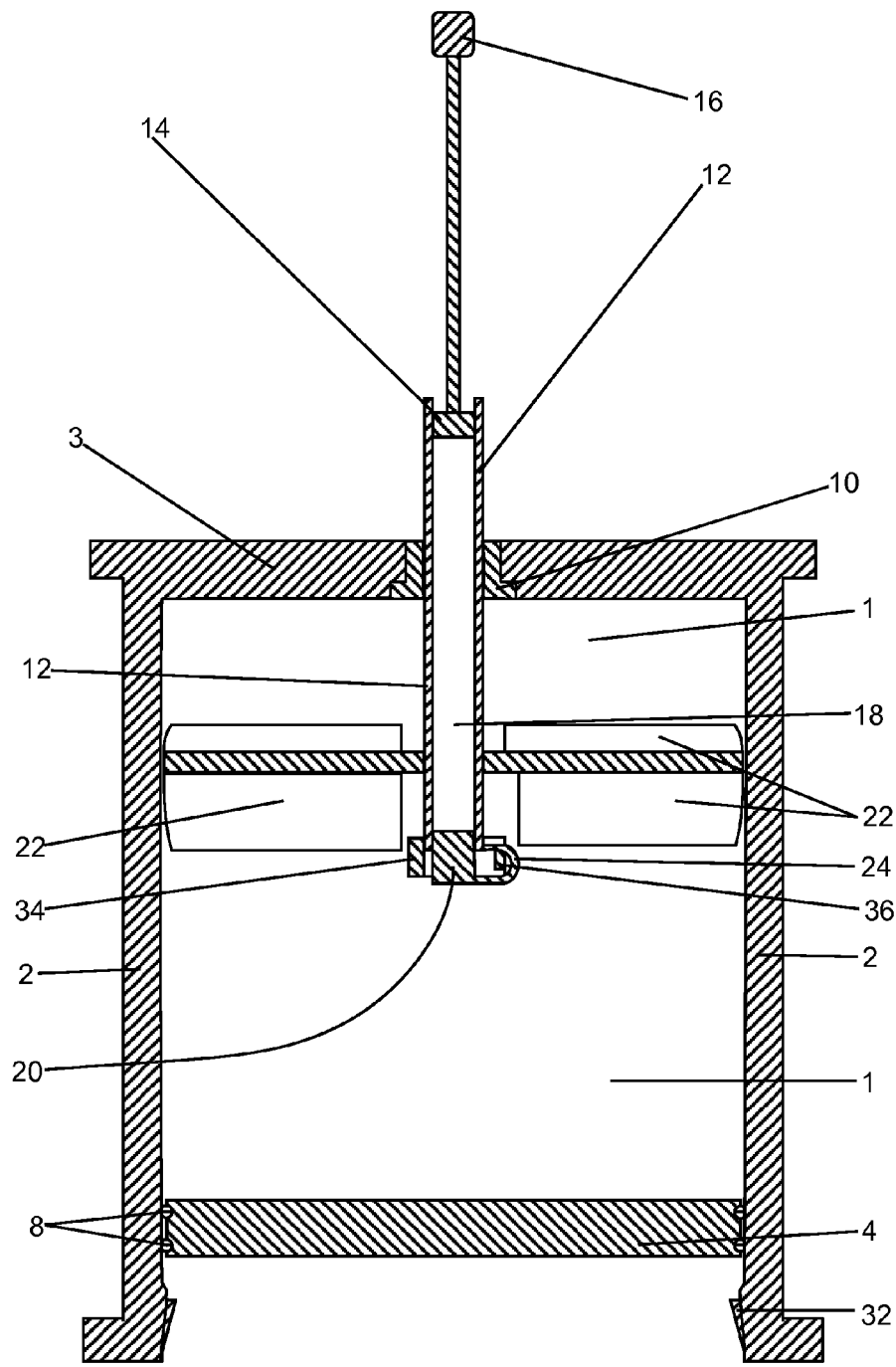
FIG. 2 shows a schematic cross-sectional view of another device according to the invention, in which a dispensing plunger is operative as volume compensation element.

FIG. 2 shows a schematic cross-sectional view of another device according to the invention, in which the dispensing plunger 4 alone serves as volume compensation element 4. The structure of the device is identical to that according to FIG. 2 except for a few details.

The device according to FIG. 2 is devoid of an additional volume compensation plunger and a lid. Instead, the plastic body 2 is simply closed on the front (on the top in FIG. 2) and forms a cover wall 3 in this location. The volume compensation through sliding in and pulling out the dispensing tube 12 proceeds exclusively through an axial motion of the dispensing plunger 4 in the present case. There is no spring element acting as a restoring element in the present embodiment.

The securing ring 34 in this embodiment comprises no extension pins, but presently is designed deep enough by means of its walls such that it, by itself, extends far enough beyond the first end of the dispensing tube 12 such that it can be slid onto the dispensing plunger 4 by pushing-on the dispensing tube 12 such that the fin 24 is pressed against the dispensing tube 12 and the plug 20 is secured. The axial recess in the securing ring 34 extends into the walls of the securing ring 34 in this case. Moreover, there again is a radial recess on the internal circumference of the securing ring 34 in this place. The remaining strut 36, which closes the securing ring 34 in this place, is elevated above the external circumference of the remaining securing ring 34 and, similar to the exemplary embodiment according to FIG. 1, is suitable for bending the fin 24 and thus for keeping the plug 20 away from the opening of the dispensing tube 12 on the first end.

The dispensing plunger 4 presently is sealed with respect to the walls 2 in gas-tight manner through two seals 8. For all other reference numbers, please refer to the description of FIG. 1.

Figure 3:
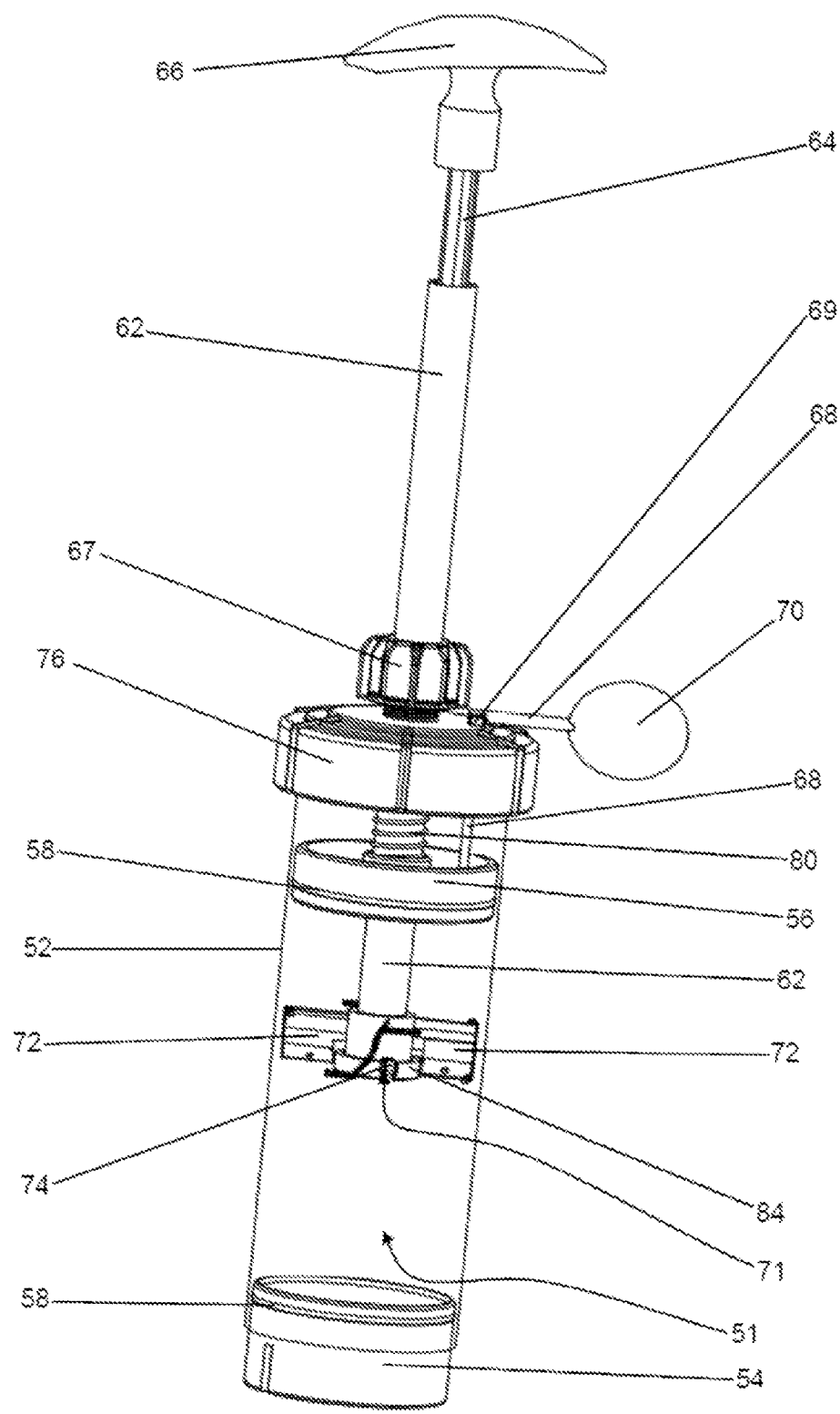
FIG. 3 shows a perspective view of a device according to the invention having a volume compensation element on its front (top)
Figure 4:
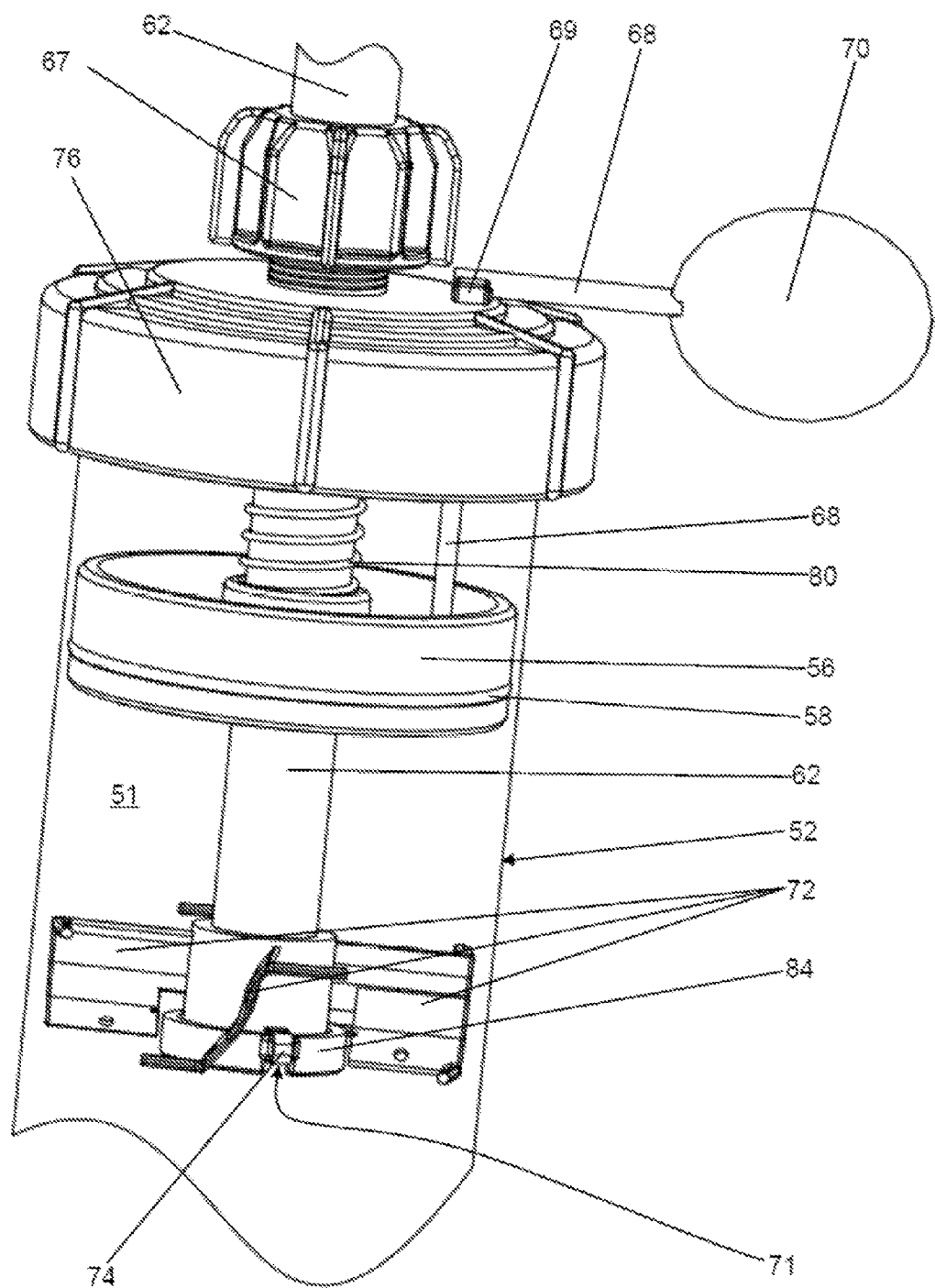
FIG. 4 shows an enlarged view of a detail of the perspective view according to FIG. 3.

FIG. 3 shows a perspective view of a device according to the invention having a volume compensation element 56 at the front (top) and FIG. 4 shows a magnified view of a detail of the perspective view according to FIG. 3. The device for storing, mixing, and applying polymethylmethacrylate bone cement shown in FIGS. 3 and 4 has a first container 51 with a cylindrical internal space that has transparent walls 52 for its boundaries. On the rear (on the bottom in FIGS. 3 and 4), the internal space of the first container 51 is closed by means of a cylindrical dispensing plunger 54 (not shown in FIG. 4) and on the front (on the top in FIGS. 3 and 4) the internal space of the first container 51 is bounded by a cylindrical volume compensation plunger 56. The dispensing plunger 54 and the volume compensation plunger 56 are arranged such as to be mobile along the cylinder axis (from top to bottom in FIGS. 3 and 4) in the internal space of the first container 51 and are sealed with respect to the internal wall of the first container 51 by means of a circumferential seal 58 each.

The front of the first container 51 is closed by a lid 76. A dispensing tube 62 projects through a feed-through on the cylinder axis of the volume compensation plunger 56 and through a feed-through through the lid 76 and extends out of the inside of the first container 51 towards the front where it exits in a dispensing opening. A core (not shown in FIGS. 3 and 4) is arranged in the dispensing tube 62 and closes the dispensing tube 62 towards the front. The core is secured to the tip of a rod 64 whose other end has a handle part 66 secured to it. The handle part 66 can be used to move the core on the inside of the dispensing tube 62. A union nut 67 can be used to affix and detach the dispensing tube 62 to and from the lid 76. In other respects, the dispensing tube 62 is mobile in longitudinal direction and is supported as in a bearing such that it can rotate with respect to the first container 51.

A locking 68 extends through an opening in the lid 76 all the way to the volume compensation plunger 56. The locking 68 is affixed with respect to the lid 76 by means of a hook 69 and a corresponding matching opposite snap-in mechanism on the locking 68 such that the volume compensation plunger 56 cannot be moved in the direction of the lid 76 or not at all relative to the lid 76 and thus to the walls 52. A handle 70 of the locking 68 can be used to detach and subsequently remove the opposite snap-in mechanism of the locking 68 from the hook 69 of the lid 76. This again renders the volume compensation plunger 56 fully mobile with respect to the lid 76. The purpose of locking the volume compensation plunger 56 is to prevent it from moving when the first container 51 is being filled with the first component and when the first container 51 is evacuated and sterilised, and to thus ease these processes.

The side of the dispensing tube 62 pointing towards the inside of the first container 51 is closed by a closure 71. The internal walls of the dispensing tube 62 and the core and the closure 71 jointly form a second container that is provided for or is filled with the second component of a cement. This end (also called first end) of the dispensing tube 62 is formed by a short sleeve that is firmly connected to the remaining dispensing tube 62. Four mixing vanes 72 are secured to said sleeve and can be moved on the inside of the first container 51 by moving the dispensing tube 62 and serve as mixing facility 72 for the content of the first container 51.

The closure 71 is connected to the sleeve and thus to the dispensing tube 62 by means of a flexible, elastic, pretensioned fin 74. Accordingly, when a pressure is exerted on the closure 71 by the core that is mediated by the second component, the closure 71 slides out of the end of the dispensing tube 62 and is moved away from the opening by the fin 74 that aims to assume a straight shape (in the relaxed state). Subsequently, the content of the second container can be transferred into the first container 51 by advancing the core.

Between the lid 76 and the volume compensation plunger 56, an elastic spring 80 is arranged about the dispensing tube 62 and establishes a definite distance between the volume compensation plunger 56 and the lid 76 in the state in which no forces are acting.

A securing ring 84 as securing element is plugged and snapped in place on the first end of the dispensing tube 62 pointing towards the inside and/or on the sleeve. The fin 74 is bent around a strut 86 of the securing ring 84, which is shown in the detailed view according to FIG. 5.

The mixing facility 72 can be used to mix the two components on the inside of the first container 51. In order to attain sufficient mixing, the mixing facility 72 needs to be actuated in the entire volume of the first container 51 and thus needs to be moved by pulling the dispensing tube 62 out and pushing it in. The volume of the content of the first container 51 changes during this process. Said volume change is taken up by the motion of the volume compensation plunger 56 since the components in the cement mixture are incompressible and no gas or only very little gas is present in the cement mixture.

Simultaneously, the first end of the dispensing tube 62 is being pushed onto the dispensing plunger 58 and the securing ring 84 is thus slid further onto the dispensing tube 62. This pushes the fin 74, by means of the strut 86, away from the opening of the dispensing tube 62 and the same applies to the closure 71. This ensures that the closure 71 does not interfere with the dispensation of the cement mixture at a later point in time.

The ready-mixed cement mixture is expelled from the first container 51 by pushing the dispensing plunger 54 in the direction of the lid 76. This can be effected by means of a suitable dispensing pistol and/or by compressed air. Before doing so, the dispensing tube 62 is pulled forward, out of the first container 51 as far as it will go such that the mixing vanes 72 touch on the inside against the volume compensation plunger 56, and the core is pulled out of the dispensing tube by means of the handle part 66, and thus the device is being opened.

Accordingly, a device according to the invention is a cement cartridge for storing, mixing, and applying a two-component cement.

Figure 5:
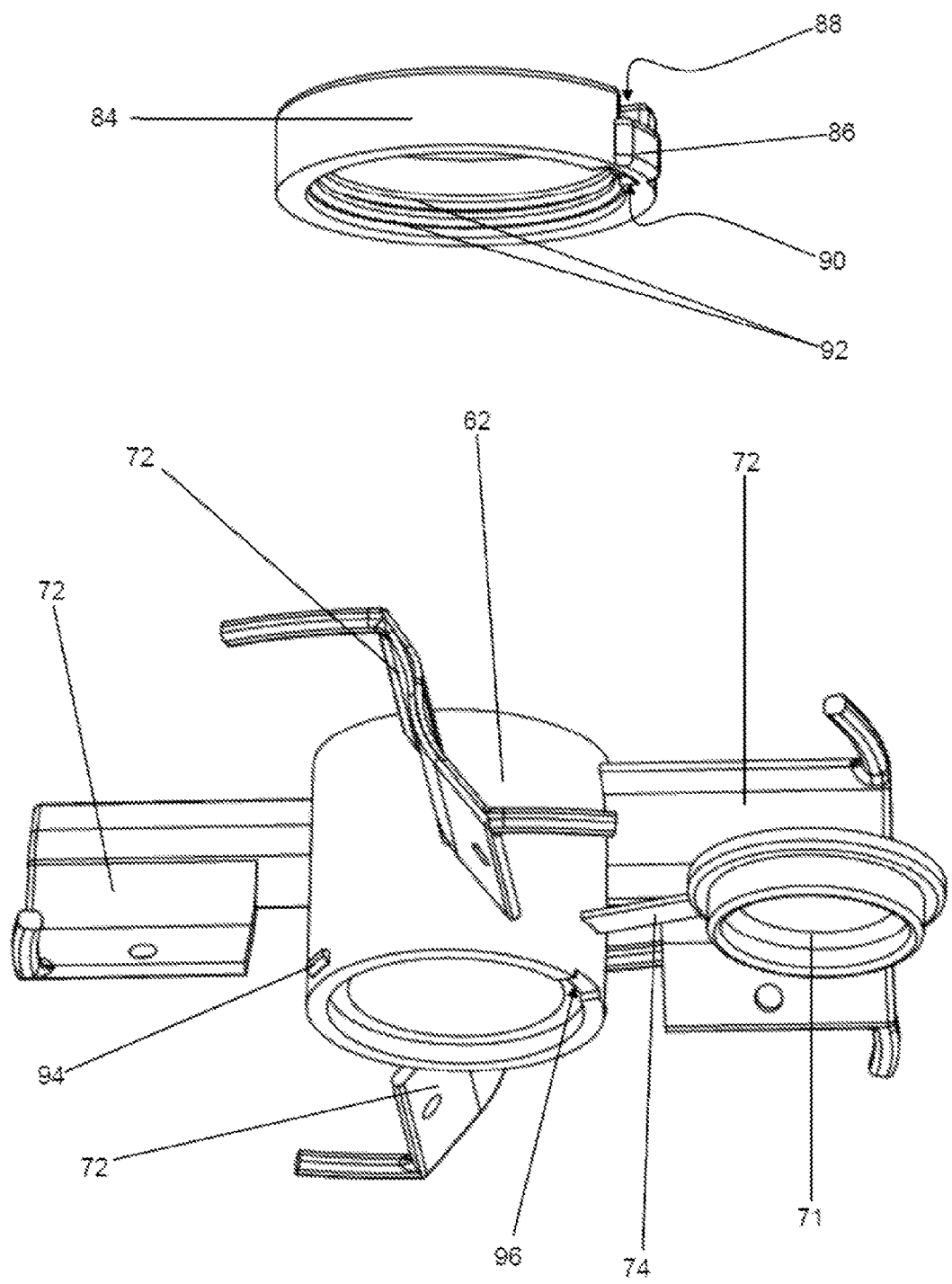
FIG. 5 shows a perspective view of the end of the dispensing tube that points into the inside of the first container and has a separate securing ring.

FIG. 5 shows a perspective view of the end of the dispensing tube 62 that points into the inside of the first container 51 and has a securing ring 84 arranged separately on it. The securing ring 84 (on the top in FIG. 5) has an axial recess 88 and a radial recess 90 that are bridged by the strut 86. Two furrows 92 or grooves 92 are arranged in the internal wall of the securing ring 84 and serve as opposite snap-in mechanism for a snap-in means 94 on the external wall of the dispensing tube 62.

The end of the dispensing tube 62 (or the sleeve as the case may be) comprises on its underside an axial recess 96 into which the fin 74 can become placed when the closure 71 closes the opening of the dispensing tube 62. The fin 74 is relaxed in the state shown in FIG. 5. During assembly of the device, the securing ring 84 is rotated by 180° perpendicular to the symmetry axis with respect to the orientation shown in FIG. 5 and plugged from below onto the first end of the dispensing tube 62 as shown until the snap-in means 94 engages the first accessible furrow 92. The strut 86 is then positioned on the fin 74. In order to prevent the securing ring from being positioned incorrectly, suitable indexing of the first end of the dispensing tube 62 and of the securing ring 84 may be provided. Subsequently, the closure 71 is folded over by 180° and plugged into the opening of the dispensing tube 62. The flexible, elastic fin 74 becomes bent around the strut 86 during this process. This results in the state of the device shown in FIGS. 3 and 4.

The essential structures according to FIGS. 1 to 5 can be manufactured easily and inexpensively from plastic materials by injection moulding technique. It is preferred to use steel springs as spring elements and/or springs. It is self-evident that the filling contents of the first container 1 and of the second container 18 do not consist of plastic material, but of the starting components of the medical cement.

The features of the invention disclosed in the preceding description and in the claims, figures, and exemplary embodiments, can be essential for the implementation of the various embodiments of the invention both alone and in any combination.

LIST OF REFERENCE NUMBERS 1, 51 First container
2, 52 Wall
3 Cover wall
4, 54 Dispensing plunger
6, 56 Volume compensation plunger/volume compensation element
8, 58 Seal
10 Guide sleeve
12, 62 Dispensing tube
14 Core
16, 66 Handle part
18 Second container
20, 71 Closure/plug
22, 72 Mixing vanes/mixing facility
24, 74 Fin
26, 76 Lid
28 Opening
30, 80 Spring
32 Snap-in mechanism
34, 84 Securing ring
36, 86 Strut
38 Extension pin
64 Rod
67 Union nut
68 Locking
69 Hook/snap-in means
70 Handle of the locking
88 Axial recess
90 Radial recess
92 Groove/opposite snap-in mechanism
94 Snap-in means
96 Axial recess

The invention claimed is:

1. A device for storing, mixing, and applying polymethylmethacrylate bone cement, the device comprises a first container for a first pasty component of the bone cement, a dispensing plunger that is arranged such that it can be shifted in the first container for pressing the content of the first container through a dispensing tube situated opposite from the dispensing plunger, whereby the dispensing tube is arranged such that it can be rotated and shifted in longitudinal direction through a feed-through in a side of the container opposite from the dispensing plunger, and a mixing facility for mixing the content of the first container, whereby the mixing facility is arranged in the first container and is secured to the dispensing tube, such that the mixing facility is movable in the first container by moving the dispensing tube to mix the content of the first container, whereby a closure that is openable is arranged on a first end of the dispensing tube pointing into the inside of the first container and closes the dispensing tube, and an axially mobile core is arranged in the dispensing tube, and a second container for at least one second component of the bone cement is formed by the space between the closure and the core in the dispensing tube, whereby the closure of the second container is removable from the first end of the dispensing tube through an axial motion of the core and thus the second container is openable with respect to the first container such that the contents of the second container and of the first container is mixable with each other in the first container, whereby at least one boundary surface of the first container is formed by a mobile volume compensation element and the closure is connected to the dispensing tube by means of a deformable connection such that the closure, even when it is open, is connected to the dispensing tube by means of the deformable connection.

2. The device according to claim 1, wherein the closure is a cap that is plugged onto or arranged on the end of the dispensing tube pointing inside or in that the closure is a stopper that is plugged into or arranged on the end of the dispensing tube pointing inside.

3. The device according to claim 1, wherein the deformable connection is a fin that is bent when the closure closes the dispensing tube, whereby the fin and the closure are optionally provided as a single part.

4. The device according to claim 1, wherein the deformable connection is tensioned and a spring force acts on the closure such as to move the closure away from the opening of the first end of the dispensing tube, when the closure is detached from the first end of the dispensing tube moving the core in axial direction.

5. The device according to claim 1, wherein a securing element is arranged on the first end of the dispensing tube pointing towards the inside of the first container and the opened closure is lockable by means of the securing element or is limited in its mobility with respect to the opening of the first end of the dispensing tube such that the opening of the first end of the dispensing tube can no longer be closed or reduced in size by the closure.

6. The device according to claim 5, wherein the securing element is a securing ring that is plugged onto the first end of the dispensing tube and that projects, in its starting state, beyond said first end and is slidable onto the first end of the dispensing tube, whereby sliding the securing ring secures the closure in that the deformability of the deformable connection is limited through the new position of the securing ring.

7. The device according to claim 1, wherein the dispensing plunger is lockable or is locked with respect to the first container, on the end of the first container opposite from the dispensing tube.

8. The device according to claim 1, wherein the first container comprises a cylindrical internal space, and the dispensing plunger in the internal space of the first container is of a shape that matches the footprint of the cylindrical internal space.

9. The device according to claim 1, wherein at least one volume compensation element, comprising the mobile volume compensation element, is arranged in or on the first container such as to be mobile in axial direction, whereby the at least one volume compensation element comprises the gas-tight feed-through through which the dispensing tube is guided in order to operate the mixing facility.

10. A device for storing, mixing, and applying polymethylmethacrylate bone cement, the device comprises a first container for a first pasty component of the bone cement, a dispensing plunger that is arranged such that it can be shifted in the first container for pressing the content of the first container through a dispensing tube situated opposite from the dispensing plunger, whereby the dispensing tube is arranged such that it can be rotated and shifted in longitudinal direction through a feed-through in a side of the container opposite from the dispensing plunger, and a mixing facility for mixing the content of the first container, whereby the mixing facility is arranged in the first container and is secured to the dispensing tube, such that the mixing facility is movable in the first container by moving the dispensing tube to mix the content of the first container, whereby a closure that is openable is arranged on a first end of the dispensing tube pointing into the inside of the first container and closes the dispensing tube, and an axially mobile core is arranged in the dispensing tube, and a second container for at least one second component of the bone cement is formed by the space between the closure and the core in the dispensing tube, whereby the closure of the second container is removable from the first end of the dispensing tube through an axial motion of the core and thus the second container is openable with respect to the first container such that the contents of the second container and of the first container is mixable with each other in the first container, whereby at least one boundary surface of the first container is formed by a mobile volume compensation element and the closure is connected to the dispensing tube by means of a deformable connection such that the closure, even when it is open, is connected to the dispensing tube by means of the deformable connection, wherein a volume compensation element is implemented by means of the dispensing plunger and in that the motion of the dispensing plunger out of the first container is limited by a boundary element, whereby the boundary element is a snap-in means engaging an opposite snap-in means on the dispensing plunger.

11. The device according to claim 1, wherein the mobile volume compensation element is arranged opposite from the dispensing plunger in the first container and is supported as in a bearing such as to be mobile, whereby the volume compensation element comprises the gas-tight feed-through for the dispensing tube.

12. The device according to claim 1, wherein the core is provided as a closure element of the dispensing opening of the dispensing tube, whereby the dispensing opening is arranged opposite from the first opening, whereby the core is removable from the dispensing tube.

13. The device according to claim 1, wherein the core comprises a wiper on the side facing the first container that wipes off powder or cement dough on the inside of the dispensing tube, when the core is being removed.

14. The device according to claim 1, wherein at least one volume compensation element, comprising the mobile volume compensation element, is supported as in a bearing through an elastic spring such as to be mobile with respect to the first container, whereby the spring moves the volume compensation element into the internal space of the first container.

15. The device according to claim 1, wherein the side of the container with the dispensing tube is closed by a closure cap comprising a feed-through for the dispensing tube, covering the mobile volume compensation element and in that the closure cap comprises at least one opening for enabling pressure equalization between the surroundings and intervening space between the closure cap and the covered volume compensation element, wherein an elastic helical spring for pushing the volume compensation element into the internal space of the first container is arranged between the closure cap and the covered volume compensation element.

16. The device according to claim 1, wherein the volume compensation element is locked by a detachable locking means.

17. A method for producing a polymethylmethacrylate bone cement using the device according to claim 1, the method comprises:
   a) providing the device according to claim 1, whereby the first container is filled with a first liquid or pasty component of the PMMA bone cement and the second container is filled with a second component of the PMMA bone cement;
   b) opening the second container by advancing the core in the dispensing tube and dispensing the second component from the second container into the first container through propelling the core further forward in the dispensing tube; and
   c) mixing the two components in the first container through moving the mixing facility, whereby moving the mixing facility is associated with the dispensing tube connected to the mixing facility being pushed into and pulled out of the first container repeatedly, whereby the volume change of the content of the first container during the mixing is compensated through a motion of the mobile volume compensation element.

18. The method according to claim 17, wherein the core is removed from the dispensing tube after step B) or after step C), and then a step D) proceeds, in which the mixed bone cement is applied by propelling the dispensing plunger forward in the first container.

19. The method according to claim 17, wherein, while the two components are being mixed in step C), the first end of the dispensing tube pointing into the inside of the first container is pushed all the way onto the dispensing plunger, whereby the pressure operates a securing element that is arranged on said first end and the operation of the securing element locks the opened closure or limits its mobility with respect to the opening of the first end of the dispensing tube appropriately such that the opening of the first end of the dispensing tube can no longer be closed or reduced in size by the closure.

20. The method according to any one of the claim 17, wherein the mixing facility is connected to the dispensing tube and the content of the first container is mixed by moving the mixing facility in the first container by moving the dispensing tube into and out of the first container, whereby, in addition, the mixing facility is being rotated by rotating the dispensing tube in the first container.

21. The method according to claim 17, wherein the first container is being filled with a component of the bone cement before step A) and the inside of the first container is first degassed and sterilised, whereby the dispensing plunger and/or the volume compensation element is locked in place for this purpose.

22. The method according to claim 17, wherein the dispensing tube, after mixing, is moved out in the direction out of the first container such that the mixing facility abuts against the inner surface of the volume compensation element or the front inner surface of the container.

23. The method according to claim 17, wherein the implementation of the method involves volume changes in the container being compensated by the volume compensation element.

* * * * *